United States Patent [19]

Teetz et al.

[11] Patent Number: 4,727,160

[45] Date of Patent: Feb. 23, 1988

[54] METHOD FOR MAKING 2-AZABICYCLO-[3.3.0]-OCTANE-3-CARBOXYLIC ACIDS

[75] Inventors: Volker Teetz, Hofheim am Taunus; Rolf Geiger, Frankfurt am Main; Hansjörg Urbach, Kronberg; Reinhard Becker, Wiesbaden; Bernward Schölkens, Kelkheim, all of Fed. Rep. of Germany

[73] Assignee: Hoechst Aktiengesellschaft, Frankfurt am Main, Fed. Rep. of Germany

[21] Appl. No.: 658,902

[22] Filed: Oct. 9, 1984

Related U.S. Application Data

[60] Division of Ser. No. 477,081, Mar. 21, 1983, abandoned, which is a continuation-in-part of Ser. No. 438,757, Nov. 3, 1982, abandoned.

[30] Foreign Application Priority Data

Nov. 5, 1981 [DE] Fed. Rep. of Germany ....... 3143946
Jul. 17, 1982 [DE] Fed. Rep. of Germany ....... 3226768

[51] Int. Cl.$^4$ ........................................... C07D 209/52
[52] U.S. Cl. .................................... 548/452; 548/454; 548/455
[58] Field of Search ...................... 548/452; 424/274; 514/412

[56] References Cited

U.S. PATENT DOCUMENTS

| | | | |
|---|---|---|---|
| 4,350,704 | 9/1982 | Hoefle et al. | 424/258 |
| 4,374,829 | 2/1983 | Harris et al. | 424/177 |
| 4,404,206 | 9/1983 | Vincent et al. | 424/258 |
| 4,470,972 | 9/1984 | Gold et al. | 424/177 |
| 4,587,258 | 5/1986 | Gold et al. | 514/412 |

FOREIGN PATENT DOCUMENTS

| | | | |
|---|---|---|---|
| 31741 | 7/1981 | European Pat. Off. | 548/515 |
| 50800 | 5/1982 | European Pat. Off. | 548/452 |
| 1955375 | 10/1971 | Fed. Rep. of Germany | |
| 2614827 | 10/1977 | Fed. Rep. of Germany | |
| 1322912 | 7/1973 | United Kingdom | |
| 761462 | 9/1980 | U.S.S.R. | 548/452 |

OTHER PUBLICATIONS

Hauptmann et al., Tetrahedron Letters (1968), 11 (1317-1319).
March, Jerry, *Advanced Organic Chemistry*, McGraw-Hill, New York (1977), p. 818.
Cervinka, Otakar, "A Transannular Reaction in the Enamme Series", Chemistry and Industry (1959) p. 1129.
J. Chem. Soc. (1959), 2087.
Chem. Ber., 92 (1959), 2218-2235.
(=Chem. Abstr. (1960), 3367g).
J. Org. Chem., 43 (1978), 54-57.
Chem. Abstr., 89, 129529w (1978).
Chem. Abstr., 89, 215732p (1978).
Tetrahedron Letters (1968), 1317-1319.
J. Chem. Soc. (1959), 1050.

*Primary Examiner*—Mary E. Ceperley
*Attorney, Agent, or Firm*—Curtis, Morris & Safford

[57] ABSTRACT

Compounds of the formula I

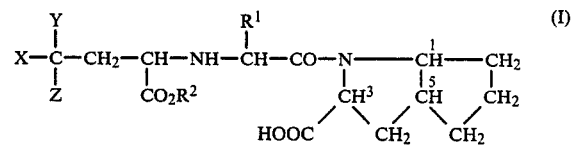

in which the carboxyl group on carbon atom 3 is orientated in the endo-position relative to the bicyclic ring system of cis-configuration, and in which $R^1$ denotes hydrogen, allyl, vinyl or a side-chain of a naturally occurring α-aminoacid, which may be protected, $R^2$ denotes hydrogen, alkyl, alkenyl or aralkyl, Y denotes hydrogen or hydroxyl and Z denotes hydrogen, or Y and Z together denote oxygen, and X denotes alkyl, alkenyl or cycloalkyl, or aryl which is optionally mono-, di- or tri-substituted by alkyl, alkoxy, hydroxyl, halogen, nitro, amino, alkylamino, dialkylamino or methylenedioxy, or denotes indol-3-yl, a process for their preparation, agents containing these compounds and their use.

2 Claims, No Drawings

METHOD FOR MAKING 2-AZABICYCLO-[3.3.0]-OCTANE-3-CARBOXYLIC ACIDS

This application is a divisional application of application Ser. No. 477,081 filed Mar. 21, 1983, now abandoned, which in turn is a continuation-in-part application of Ser. No. 438,757 filed Nov. 3, 1982 and now abandoned.

The invention relates to cis, endoazabicyclo-[3.3.0]-octanecarboxylic acids of the formula I

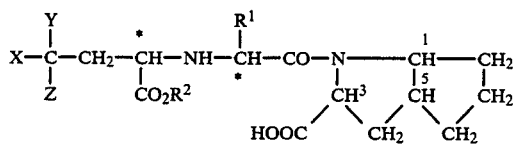

in which the hydrogen atoms on the bridge-head carbon atoms 1 and 5 are in the cis-configuration relative to one another and the carboxyl group on carbon atom 3 is orientated in the endo-position relative to the bicyclic ring system, and in which $R^1$ denotes hydrogen, allyl, vinyl or a side-chain of a naturally occurring α-aminoacid $R^1$—CH(NH$_2$)—COOH, which may be protected, $R^2$ denotes hydrogen, ($C_1$–$C_6$)-alkyl, ($C_2$–$C_6$)-alkenyl or ($C_6$–$C_{12}$)-aryl-($C_1$–$C_4$)-alkyl, which can be mono-substituted by nitro, Y denotes hydrogen or hydroxyl and Z denotes hydrogen, or Y and Z together denote oxygen, and X denotes ($C_1$–$C_6$)-alkyl, ($C_2$–$C_6$)-alkenyl or ($C_5$–$C_9$)-cycloalkyl, or ($C_6$–$C_{12}$)-aryl, preferably phenyl, which can be mono-, di- or tri-substituted by ($C_1$–$C_4$)-alkyl, ($C_1$–$C_4$)-alkoxy, hydroxyl, halogen, nitro, amino, ($C_1$–$C_4$)-alkylamino, di-($C_1$–$C_4$)-alkylamino and/or methylenedioxy, or denotes indol-3-yl, and physiologically acceptable salts thereof.

Compounds of the formula I in which $R^1$ denotes methyl, the side-chain of lysine, which may be acylated, or the O-($C_1$–$C_6$)-alkylated side-chain of tyrosine, $R^2$ denotes hydrogen, methyl, ethyl or benzyl, X denotes phenyl, or phenyl which is mono- or di-substituted by fluorine and/or chlorine, Y denotes hydrogen or hydroxyl and Z denotes hydrogen, or Y and Z together denote oxygen, are preferred.

Naturally occuring α-aminoacids are, for example, Ala, Val, Leu, Ile, Phe, Ser, Thr, Lys, Hyl, Arg, Asp, Asn, Glu, Gen, Cys, Met, Tyr, Pro, Hyp, Trp, His, Orn and Cit.

In this context and in the following text ($C_6$–$C_{12}$)-aryl is to be understood as meaning preferably biphenylyl, naphthyl, or especially phenyl.

If $R^1$ represents a side-chain of a protected naturally occurring α-aminoacid, such as, for example, protected Ser, Thr, Asp, Asn, Glu, Gln, Arg, Lys, Hyl, Cys, Orn, Cit, Tyr, Trp, His or Hyp, the groups customary in peptide chemistry are preferred as protective groups (cf. Houben-Weyl, Volume XV/1 and XV(2)). In the case where $R^1$ denotes the protected lysine side-chain, the known amino-protective groups are preferred, especially ($C_1$–$C_6$)-alkanoyl. Preferred O-protective groups for tyrosine are methyl or ethyl.

The compounds of formula I, having both acidic and basic groups, are amphoteric compounds. Electrically neutral moleculs of I exist in the form of zwitterions.

An acidic group is especially the 3-carboxy group. If $R^2$ denotes hydrogen and/or $R^1$ denotes a side-chain of a acidic aminoacid (e.g. Glu, Asp) two or three additional acidic groups are present in the molecule. Di- and tribasic acids of formula I can form acidic (hydrogen) salts by partial neutralisation of the acid. Particularly suitable base addition salts are alkali metal salts and alkaline earth metal salts (for example Ca, Mg and Zn salts), and salts with physiologically tolerated amines.

A basic group is especially the —NH-group in the main chain. If X denotes ($C_6$–$C_{12}$)-aryl which is substituted by amino, alkylamino or dialkylamino and/or $R^1$ denotes a side chain of a basic amono acid (e.g. Arg, Lys, Hyl, Orn, Cit, His) two or more basic groups are present in the molecule. Compounds of formula I having two or more basic groups can form normal salts wherein all the basic groups are neutralised, but also salts by partial neutralisation of these groups.

Particularly suitable acid addition salts are salts with physiologically tolerable inoroganig or organic acids, such as, for example HCl, HBr, H$_2$SO$_4$, H$_3$PO$_4$, maleic acid, fumaric acid and tartaric acid.

the chirality centers on the carbon atoms laebeled with a star (*) in the chain and on carbon atom 3 of the bicyclic ring system can have either the R-configuration or the S-configuration. However, compounds in which these centers are in the S-configuration are preferred. If —NH—*CHR$^1$—CO— represents Cys, however, the R-configuration of this center is preferred.

The invention furthermore relates to a process for the preparation of the compounds of the formula I, which comprises reacting a compound of the formula II in which $R^2$ has the abovementioned meanings, with the exception of hydrogen, with a compound of the formula IIIa or IIIb, in which W denotes a carboxyl-esterifying group, such as ($C_1$–$C_6$)-alkyl or ($C_7$–$C_8$)-aralkyl (e.g. benzyl, phenethyl or xylyl) preferably tert.-butyl or benzyl, by the known amide formation methods of peptide chemistry, and then liberating the compounds of type I by hydrogenation or treatment with an acid or-/and base.

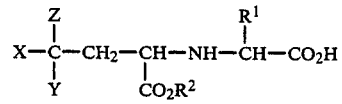

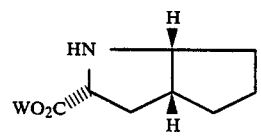

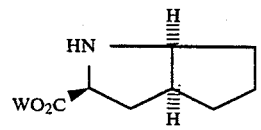

Compounds of the formula II in which X is phenyl, Y is H, Z is H and $R^2$ is CH$_3$ or C$_2$H$_5$ are known (for example from European Pat. No. 0,037,231), and are accessible in various ways. The benzyl ester ($R^2$=benzyl) can be prepared analogously.

It has furthermore been found that the Mannich reaction of acetophenones of the formula IVa, in which X represents aryl which is optionally substituted as described above, with glyoxylic acid esters and α-aminoacid esters leads to compounds of the formula II in which Y and Z together denote oxygen (formula IV). In formula IV, W' denotes a radical which can be split off by basic or acidic hydrogenolysis, preferably benzyl or tert.-butyl, X represents aryl which is optionally substituted as described above and $R^1$ and $R^2$ have the above-mentioned meanings. However, in the case of the benzyl ester (W'=benzyl), $R^2$ may not be benzyl. Hydrogenolysis of these compounds with Pd gives compounds of the formula II in which Y and Z are hydrogen.

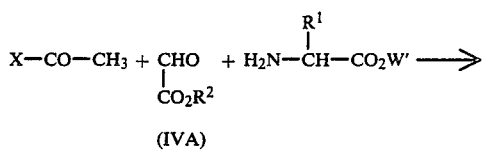

(IVA)

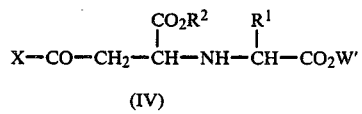

(IV)

Compounds of the formula II in which Y and Z together denote oxygen can also be obtained in high yields by Michael addition of corresponding keto-acrylic acid esters with α-aminoacid esters. Ester cleavage leads to the same products as the Mannich reaction.

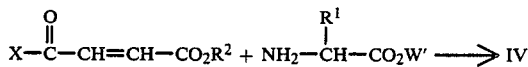

When L-alanine esters are used, the diastereomers with the preferred S,S-configuration are predominantly formed, and can be isolated by crystallization or by chromatographic separation of the esters of II on silica gel.

It has furthermore been found that cis,endo-2-azabicyclo[3.3.0]octane-3-carboxylic acid esters of the formulae III a and b are accessible from enamines of cyclopentanone of the formula VI, in which $X^1$ represents dialkylamino with 2 to 10 carbon atoms or a radical of the formula VII, in which m and o denote integers from 1 to 3, (m+o)≧3 and A denotes $CH_2$, NH, O or S,

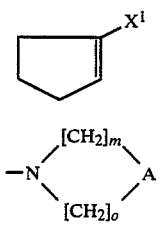

and N-acylated β-halogeno-α-amino-carboxylic acid esters of the formula VIII, in which $X^2$ represents a nucleofugic group, preferably chlorine or bromine, $Y^1$ represents alkanoyl with 1 to 5 carbon atoms, aroyl with 7 to 9 carbon atoms or other protective groups which are customary in peptide chemistry and can be split off under acid conditions, and $R^2$ represents alkyl with 1 to 5 carbon atoms or aralkyl with 7 to 9 carbon atoms

or with acrylic acid esters of the formula IX, in which $Y^1$ and $R^2$ have the above meanings,

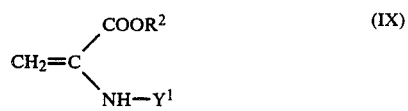

by reacting these starting materials to give compounds of the formula X, in which $R^2$ and $Y^1$ have the above meanings,

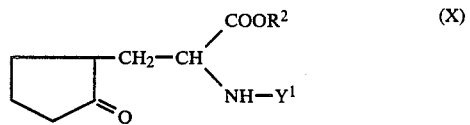

cyclizing these compounds with the aid of strong acids, with acylamide and ester cleavage, to give compounds of the formula XI a or b

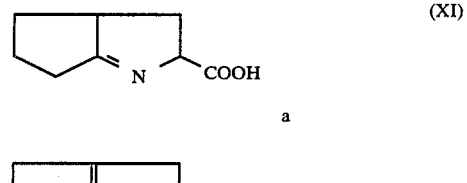

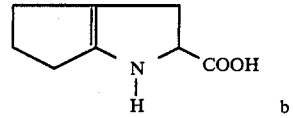

converting these into compounds of the formula IIIa or b, in which W represents hydrogen, by catalytic hydrogenation in the presence of transition metal catalysts or by reduction with borane-amine complexes or complex borohydrides in lower alcohols, and optionally esterifying the products to give compounds of the formula III a or b in which W represents alkyl with 1 to 6 carbon atoms or aralkyl with 7 to 8 carbon atoms.

The bicyclic aminoacids of the formulae IIIa and b have the cis,endo-configuration, i.e. the —$CO_2W$ group faces the cyclopentane ring. All the other 2-azabicyclo[3.3.0]-octane-3-carboxylic acid derivatives mentioned in the present invention are also in the cis,endo-configuration.

Examples of preferred enamines are pyrrolidinocyclopentene and morpholinocyclopentene. Cyclization of the alkylation products of the formula X is preferably carried out with aqueous hydrochloric acid. The compounds of the formula III (in which W is H) can be esterified by the methods customary for aminoacids (cf. for example, Houben-Weyl, Methoden der organischen Chemie (Methods of Organic Chemistry), Volume VIII (1952)), for example with thionyl chloride/benzyl alcohol or isobutylene/sulfuric acid. They give, after appropriate working up, compounds of the formula III in the form of the free base or of a salt.

The new compounds of the formula I have a longlasting, intense hypotensive action. They are powerful inhibitors of the angiotension-converting enzyme (ACE inhibitors) and can be used for controlling high blood pressure of various origins. They can also be combined with other hypotensive, vasodilating or diuretic compounds. Typical representatives of these classes of active compounds are described in, for example, Erhardt-Ruschig, Arzneimittel (Medicaments), 2nd edition, Weinheim, 1972. They can be administered intravenously, subcutaneously or perorally. The dosage for oral administration is 1–100, preferably 1–50, especially 1–30 mg per individual dose for an adult of normal body weight, i.e. 13–1300 μg/kg/day, preferably 13–650 μg/kg/day, especially 13–400 μg/kg/day. In severe cases, it can also be increased, since no toxic properties have as yet been observed. It is also possible to reduce the dose, which is appropriate, above all, if diuretic agents are administered at the same time.

The compounds according to the invention can be administered orally or parenterally in an appropriate pharmaceutical formulation. For an oral use form, the active compounds are mixed with the additives customary for this form, such as excipients, stabilizers or inert diluents, and the mixture is converted to suitable administration forms, such as tablets, dragees, push-fit capsules, aqueous alcoholic or oily suspensions or aqueous alcoholic or oily solutions, by customary methods. Examples of inert carriers which can be used are gum arabic, magnesium stearate, potassium phosphate, lactose, glucose and starch, especially maize starch. The formulation may be prepared in the form of either dry or moist granules. Examples of possible oily excipients or solvents are vegetable and animal oils, such as sunflower oil /or cod-liver oil.

For subcutaneous or intravenous administration, the active compounds or physiologically acceptable salts thereof are dissolved, suspended or emulsified, if desired with the substances customary for this purpose, such as solubilizing agents, emulsifiers or other auxiliaries. Examples of possible solvents for the new active compounds and the corresponding physiologically acceptable salts are: water, physiological sodium chloride solutions or alcohols, for example ethanol, propanediol or glycerol, and in addition also sugar solutions, such as glucose or mannitol solutions, or a mixture of the various solvents mentioned.

The exceptionally powerful activity of the compounds according to the formula I—even when administered orally—is demonstrated by the following pharmacological data.

1. Intravenous administration to anesthetized rats, 50% inhibition of the pressor reaction induced by 310 ng of angiotensin I, 30 minutes after administration of the dose . . . $ED_{50}$

| X | Y | Z | $R^1$ | $R^2$ | $ED_{50}$ (μg/kg) |
|---|---|---|---|---|---|
| $C_6H_5$ | H | H | $CH_3$ | $C_2H_5$ | 8.3 |
| $C_6H_5$ | H | H | $CH_3$ | H | 2.7 |

2. Intraduodenal administration to anesthetized rats

| X | Y | Z | $R^1$ | $R^2$ | $ED_{50}$ (μg/kg) |
|---|---|---|---|---|---|
| $C_6H_5$ | H | H | $CH_3$ | $C_2H_5$ | 50 |
| $C_6H_5$ | H | H | $CH_3$ | H | 600 |
| $C_6H_5$ | — | O | $CH_3$ | $CH_3$ | 350 |
| $C_6H_5$ | — | O | $CH_3$ | $C_2H_5$ | 280 |
| $C_6H_5$ | — | O | $CH_3$ | H | 720 |
| $C_6H_5$ | — | O | $CH_3$ | $C_7H_7$ | 250 |
| $C_6H_5$ | H | OH | $CH_3$ | $C_2H_5$ | 380 |
| p-Cl—$C_6H_4$ | H | H | $CH_3$ | $C_2H_5$ | 55 |
| p-Cl—$C_6H_4$ | — | O | $CH_3$ | H | 780 |

3. On oral administration to conscious rats, a dosage of 1 mg/kg of, for example, the compound of the formula I in which X is phenyl, Y and Z are each H, $R^1$ is $CH_3$ and $R^2$ is ethyl exhibits 90% inhibition, lasting over 6 hours, of the pressor reaction triggered off by intravenous administration of angiotensin I.

The Examples which follow are intended to illustrate the procedures according to the invention, without restricting the invention to the substances mentioned here as representatives.

EXAMPLE I

N-(1-S-Carbethoxy-3-phenyl-propyl)-S-alanyl-2-cis,endoazabicyclo-[3.3.0]-octane-3-S-carboxylic acid (1) Methyl 2-acetylamino-3-(2-oxo-cyclopentyl)-propionate:

269 g of methyl 3-chloro-2-acetylamino-propionate and 257 g of cyclopentenopyrrolidine in 1.5 liters of dimethylformamide were kept at room temperature for 24 hours. The mixture was concentrated in vacuo, the residue was taken up in a little water and the aqueous mixture was adjusted to pH 2 with concentrated hydrochloric acid and extracted twice with 4 liter portions of ethyl acetate. On concentration of the organic phase, a light yellow oil remained.

Yield: 290 g.

NMR: 2.02 (s, 3H); 3.74 (s 3H); 4.4–4.8 (m, 1H) (CDCl$_3$).

| Analysis: | C | H | N |
|---|---|---|---|
| calculated | 58.1 | 7.54 | 6.16 |
| found | 58.5 | 7.2 | 6.5 |

(2) cis,endo-2-Azabicyclo-[3.3.0]-octane-3-carboxylic acid hydrochloride 270 g of the acetylamino derivative prepared under (1) were boiled under reflux in 1.5 liters of 2N hydrochloric acid for 45 minutes. The mixture was concentrated in vacuo, the residue was taken up in glacial acetic acid, 5 g of Pt/C (10% of Pt) were added and hydrogenation was carried out under 5 bar. After filtration, the mixture was concentrated and the residue was crystallized from chloroform/diisopropyl ether.

Melting point: 205°–209° C.

Yield: 150 g.

(3) Benzyl cis,endo-2-azabicyclo-[3.3.0]-octane-3-carboxylate hydrochloride 40 g of the carboxylic acid prepared under (2) were added to an ice-cold mixture of 390 g of benzyl alcohol and 65 g of thionyl chloride and the mixture was left to stand at room temperature for 24 hours. After concentration in vacuo, 47 g of the benzyl ester were crystallized from chloroform/isopropanol.

Melting point: 175° C. (hydrochloride).

(4) Benzyl N-(2-S-carbethoxy-3-phenyl-propyl)-S-alanyl-cis,endo-2-azabicyclo-[3.3.0]-octane-3-S-carboxylate 14 g of the benzyl ester prepared according to (3) were reacted with 6.7 g of HOBt, 13.8 g of N-(1-S-carbethoxy-3-phenyl-propyl)-S-alanine and 10.2 g of dicyclohexylcarbodiimide in 200 ml of dimethylformamide. After the mixture had been stirred for 3 hours at room temperature, the dicyclohexylurea which had precipitated was filtered off with suction, the filtrate was concentrated, the residue was taken up in 1 liter of ethyl acetate and the mixture was extracted by shaking with $3 \times 500$ ml of 5 percent strength $NaHCO_3$ solution. The organic phase was concentrated and the residue was chromatographed over a column of 1 kg of silica gel using ethyl acetate/petroleum ether in the ratio 2:1. The isomer eluted first was the S,S,S-compound, and concentration of a later eluate gave the S,S,R-compound.

In each case 8.0 g of product were obtained as an oil. NMR: of the S,S,S-compound: characteristic signals: 1.20 (d, 3H), 1.27 (t, 2H), 4.17 (q, 3H), 5.13 (s, 2H), 7.18 (s, 5H) and 7.32 (s, 5H) ($CDCl_3$).

| Analysis | | C | H | N |
|---|---|---|---|---|
| $C_{30}H_{38}N_2O_5$ | calculated | 71.1 | 7.56 | 5.53 |
| | found | 70.8 | 7.8 | 5.7 |

(5) N-(1-S-Carbethoxy-3-phenyl-propyl)-S-alanyl-cis,endo-2-azabicyclo-[3.3.0]-octane-3-S-carboxylic acid 8.0 g of the L,L,L-benzyl ester from (4) were dissolved in 100 ml of ethanol and were debenzylated hydrogenolytically under normal pressure, with addition of 0.5 g of 10% Pd/C. This reaction could also have been carried out under pressure, together with a shortening of the reaction time. After the calculated amount of hydrogen had been taken up, the catalyst was filtered off and the residue was concentrated in vacuo. The zwitter ion crystallized from ether, in almost quantitative yield. Melting point: 110°-112° C. (decomposition)

A hydrochloride (decomposition from 120° C.) can be obtained by addition of an equivalent amount of hydrochloric acid, or a zinc complex salts which is particularly stable to heat (decomposition above 160° C.) can be obtained by addition of aqueous zinc salts to a concentrated methanolic solution of the title compound.

| Analysis | | C | H | N |
|---|---|---|---|---|
| $C_{23}H_{32}N_2O_5$ | calculated | 66.3 | 7.7 | 6.73 |
| | found | 66.1 | 7.8 | 6.6 |

The NMR and mass spectra obtained are in agreement with the given structure.

$[\alpha]_D = +15.6°$ (c=1, methanol).

EXAMPLE II (1) tert.-Butyl cis,endo-2-azabicyclo-[3.3.0]-octane-3-carboxylate 25 g of azabicyclo-[3.3.0]-octane-carboxylic acid hydrochloride from Example I(2) were reacted with 250 ml of isobutylene and 25 ml of concentrated sulfuric acid in 250 ml of dioxane. After 14 hours at room temperature, the mixture was rendered alkaline with sodium hydroxide solution and concentrated in vacuo, 100 ml of water were added and the ester was extracted with ether. Evaporation of the ether gave 15 g of a colorless oil.

| Analysis | | C | H | N |
|---|---|---|---|---|
| $C_{12}H_{21}NO_2$ | calculated | 68.2 | 10.2 | 6.63 |
| | found | 67.9 | 10.1 | 6.3 |

(2) N-(1-S-Carbobenzyloxy-3-oxo-3-phenyl-propyl)-S-alanine tert.-butyl ester 12.0 g of acetophenone, 17 g of benzyl glyoxylate and 31.7 g of alanine tert.-butyl ester toluenesulfonate were heated to 45°-50° C. in 200 ml of glacial acetic acid for 24 to 48 hours. The reaction was monitored by thin layer chromatography and was interrupted at the optimum reaction point. The mixture was concentrated thoroughly in vacuo, the residue was rendered basic with aqueous bicarbonate solution and the mixture was extracted with ethyl acetate. The organic phase was concentrated as substantially as possible and the S,S-isomer was crystallized from cyclohexane/petroleum ether. The R,S-compound remained substantially in solution. To obtain seed crystals, chromatography of the crude mixture on silica gel in a 2:1 cyclohexane:ethyl acetate system to which 0.1% of triethylamine had been added was advisable. The S,S-compound was eluted as the second of the two diastereomers and was obtained in the larger amount. 9 g were obtained.

| Analysis | | C | H | N |
|---|---|---|---|---|
| $C_{24}H_{29}NO_5$ | calculated | 70.1 | 7.1 | 3.4 |
| | found | 70.0 | 6.9 | 3.5 |

(3) N-(1-S-Carbobenzyloxy-3-oxo-3-phenyl-propyl)-S-alanine trifluoroacetate 8 g of the Mannich condensation product from (2) were dissolved in 25 ml of anhydrous trifluoroacetic acid and the solution was left at room temperature for one hour. The solution was concentrated in vacuo, diisopropyl ether was added and the product was precipitated with petroleum ether. 7.2 g of an amorphous substance were obtained.

| Analysis | | C | H | N |
|---|---|---|---|---|
| $C_{22}H_{22}NO_7F_3$ | calculated | 56.3 | 4.7 | 3.0 |
| | found | 56.0 | 4.8 | 3.1 |

Molecular weight: 469.

(4) tert.-Butyl N-(1-S-carbobenzyloxy-3-oxo-3-phenyl-propyl)-S-alanyl-2-cis,endo-azabicyclo-[3.3.0]-octane-3-carboxylate 35.5 g of the N-substituted alanine from (3) were reacted with 21.1 g of the tert.-butyl azabicyclooctanecarboxylate from Example II(1) analogously to Example I(4). Chromatography over silica gel gave 20.3 g of the title compound.

| Analysis | | C | H | N |
|---|---|---|---|---|
| $C_{32}H_{40}N_2O_6$ | calculated | 70.04 | 7.35 | 5.10 |
| | found | 69.6 | 7.4 | 5.3 |

(5) N-(1-S-Carbobenzyloxy-3-oxo-3-phenyl-propyl)-S-alanyl-2-cis,endo-azabicyclo-[3.3.0]-octane-3-carboxylic acid 20 g of the tert.-butyl ester from (4) were dissolved in 100 ml of trifluoroacetic acid and the solution was left to stand at room temperature for one hour. The solution was concentrated in vacuo, the resin which remained was taken up in ethyl acetate and the mixture was neutralized with aqueous bicarbonate. 14 g of the title compound were obtained from the ethyl acetate phase.

| Analysis | | C | H | N |
| --- | --- | --- | --- | --- |
| $C_{28}H_{32}N_2O_6$ | calculated | 68.27 | 6.55 | 5.69 |
| | found | 68.1 | 6.4 | 5.7 |

(6) N-(1-S-Carboxy-3-R,S-hydroxy-3-phenyl-propyl)-S-alanyl-cis,endo-2-azabicyclo-[3.3.0]-octane-3-carboxylic acid 1 g of N-(1-S-carbobenzyloxy-3-oxo-3-phenyl-propyl)-S-alanyl-cis,endo-2-azabicyclo-[3.3.0]-octane-3-carboxylic acid were dissolved in 50 ml of ethanol, 150 mg of $Pd/BaSO_4$ were added and hydrogenation was carried out under normal pressure. After the calculated amount of hydrogen had been taken up, the mixture was filtered, the filtrate was concentrated and the residue was chromatographed over silica gel in the solvent $CHCl_3/CH_3OH/CH_3COOH$ 50:20:5.

Yield: 0.6 g.

(7) N-(1-S-Carbobenzyloxy-3-R,S-hydroxy-3-phenyl-propyl)-S-alanyl-cis,endo-2-azabicyclo-[3.3.0]-octane-3-carboxylic acid 1 g of N-(1-S-carbobenzyloxy-3-oxo-3-phenyl-propyl)-S-alanyl-2-cis,endo-azabicyclo-[3.3.0]-octane-3-carboxylic acid were dissolved in 50 ml of a mixture of acetonitrile and water and were reduced with 150 mg of $NaBH_4$. After 12 hours, the mixture was concentrated to dryness, the residue was rendered neutral with dilute hydrochloric acid and the title compound was extracted with ethyl acetate. To remove boric acid and other impurities, the product was chromatographed over silica gel in the solvent $CHCl_3/CH_3OH/CH_3COOH$ 50:10:5.

| Analysis | | C | H | N |
| --- | --- | --- | --- | --- |
| $C_{28}H_{34}N_2O_6$ | calculated | 67.99 | 6.93 | 5.66 |
| | found | 67.7 | 6.6 | 5.3 |

EXAMPLE III

General method: Hydrolysis of esters to prepare compounds of the formula I in which $R^2$ is H.

10 g of the corresponding ethyl or benzyl ester of the formula I were dissolved in 200 ml of dimethoxyethane. One drop of a dilute indicator solution, for example bromothymol blue, was added, and an equivalent amount of 4N KOH (aqueous) was added in the course of 5 minutes, while stirring vigorously, so that at the end of the reaction the indicator indicated a pH value of 9–10. The mixture was then adjusted to pH 4 with hydrochloric acid and concentrated to dryness in vacuo, the residue was taken up in 250 ml of ethyl acetate and the mixture was filtered. On concentration of the ethyl acetate, the dicarboxylic acids precipitated as solid, crystalline or amorphous compounds.

The yields were between 80 and 95%.

EXAMPLE IIIa

N-(1-S-Carboxy-3-phenyl-propyl)-S-alanyl-cis,endo-2-azabicyclo-[3.3.0]-octane-3-S-carboxylic acid 1 g of N-(1-S-carbethoxy-3-phenyl-propyl)-S-alanyl-2-azabicyclo-[3.3.0]-octane-3-S-carboxylic acid from Example I(5) was hydrolyzed (1 hour) and the mixture was worked up, as described under Example III.

Yield: 0.85 g.

m/e: 388.

EXAMPLE IV

N-(1-S-Carbethoxy-3-oxo-3-phenyl-propyl)-S-alanine benzyl ester 65.7 g of ethyl 4-phenyl-4-oxo-butene-2-carboxylate (ethyl benzoylacrylate) were dissolved in 225 ml of ethanol, and 1 ml of triethylamine was added. A solution of 70 g of S-alanine benzyl ester in 90 ml of ethanol was rapidly added dropwise at room temperature. The mixture was stirred at room temperature for 2 hours and the solution was then cooled. The S,S-isomer crystallized out.

Yield: 94.3 g. Melting point: 83°–74° C.

$[\alpha]_D^{20} = +17.8°$ (c=1, $CH_3OH$).

EXAMPLE V

N-(1-S-Carbethoxy-3-oxo-3-phenyl-propyl)-S-alanine 0.5 g of the compound from Example IV was dissolved in 40 ml of ethanol, 0.1 g of 10% Pd/C was added and hydrogenation was carried out at room temperature and under normal pressure.

Yield: 300 mg. Melting point: 210°–220° C.

$^1$H-NMR (DMSO-$d_6$): 1.0–1.4 (t, 6H); 3.2–5.0 (m, 8H); 7.2–8.2 (m, 5H).

EXAMPLE VI

Benzyl N-(1-S-carbethoxy-3-oxo-3-phenyl-propyl)-S-alanyl-cis,endo-2-azabicyclo-[3.3.0]-octane-3-S-carboxylate The compound was prepared from benzyl cis,endo-2-azabicyclo-[3.3.0]-octane-3-S-carboxylate hydrochloride and N-(1-S-carbethoxy-3-oxo-3-phenyl-propyl)-S-alanine from Example V, analogously to the process described in Example I(4).

EXAMPLE VII

N-(1-S-carbethoxy-3-oxo-3-phenyl-propyl)-S-alanyl-cis,endo-2-azabicyclo-[3.3.0]-octane-3-S-carboxylic acid 1 g of the benzyl ester from Example VI was dissolved in 30 ml of ethanol and hydrogenated with 100 mg of Pd/C (10%) at room temperature and under normal pressure. After one mole equivalent of hydrogen had been taken up, the hydrogenation was interrupted. The catalsyt was filtered off with suction and the solution was concentrated.

Yield: 600 mg of an oil.

$^1$H-NMR (DMSO-$d_6$): 1.0–3.0 (m, 15H); 3.3–5.0 (m, 10H); 7.2–8.1 (m, 5H).

EXAMPLE VIII

N$_\alpha$-(1-S-Carbethoxy-3-phenyl-propyl)-S-lysyl-cis,endo-2-azabicyclo-[3.3.0]-octane-3-S-carboxylic acid dihydrochloride (1) N$_\alpha$-(1-S-Carbethoxy-3-oxo-3-phenyl-propyl)-N$_\epsilon$-benzyloxycarbonyl-S-lysine benzyl ester 10 g of ethyl 4-phenyl-4-oxo-butene-2-carboxylate were dissolved in 100 ml of ethanol. 19.1 g of N$_\epsilon$-benzyloxycarbonyl-S-lysine benzyl ester and 0.2 g of triethylamine were added. The solution was stirred at room temperature for 3 hours and was then concentrated in vacuo. The oily residue (31 g) was dissolved in isopropanol/diisopropyl ether and the solution was cooled. 13 g of N$_\alpha$-(1-S-carbethoxy-3-oxo-3-phenyl-propyl)-N$_\epsilon$-benzyloxycarbonyl-S-lysine benzyl ester crystallized.

$\alpha_D^{20}=3.5°$ (c=1, CH$_3$OH).

$^1$H-NMR (CDCl$_3$): 1.0–1.4 (tr, 3H); 1.0–2.0 (m, 9H); 2.0–2.6 (broad, s., 1H); 2.9–3.9 (m, 6H); 3.9–4.4 (quadr. 2H); 4.6–4.9 (broad s., 1H); 5.0–5.2 (double s., 4H) 7.1–8.1 (m, 15H).

(2) N$_\alpha$-(1-S-Carbethoxy-3-phenyl-propyl)-N$_\epsilon$-benzyloxycarbonyl-S-lysine 4.0 g of the lysine benzyl ester derivative prepared in Example VIII(1) were dissolved in 50 ml of glacial acetic acid, and 0.6 g of Pd/C (10%) and 0.6 g of concentrated sulfuric acid were added. Hydrogenation was carried out at room temperature and under normal pressure for 6 hours. The catalyst was then filtered off with suction and the ethanolic solution was stirred with 1.4 g of solid sodium bicarbonate. The solution was concentrated on a rotary evaporator and the residue was dissolved in water. The aqueous phase was extracted with ethyl acetate and methylene chloride. The organic phases were discarded and the aqueous phase was evaporated to dryness in vacuo. The residue was extracted by stirring with methanol. After the methanol had been evaporated off, an oily residue remained, which solidified when treated with diisopropyl ether. Yield of N$_\alpha$-(1-S-carbethoxy-3-phenyl-propyl)-S-lysine: 2.0 g.

$^1$H-NMR (D$_2$O): 1.0–1.4 (tr, 3H); 1.0–2.5 (m, 9H), 2.5–4.4 (m, 9H); 3.9–4.4 (q, 2H); 4.5–5.0 (m, 1H); 7.1–7.6 (m, 5H).

m/e: 336.

3.4 g of N$_\alpha$-(1-S-carbethoxy-3-phenyl-propyl)-S-lysine were dissolved in 30 ml of methylene chloride and the solution was cooled to 0° C. While cooling with ice, 2.1 g of triethylamine were added, and 1.9 g of benzyl chloroformate were then added dropwise. The mixture was stirred at 0° C. for 1 hour and was then brought to room temperature. The methylene chloride solution was extracted by shaking successively with water, sodium carbonate solution and water. After the product phase had been dried, it was concentrated and the oily residue was chromatographed over silica gel using methylene chloride/methanol. 2.0 g of N$_\alpha$-(1-S-carbethoxy-3-phenyl-propyl)-N$_\epsilon$-benzyloxycarbonyl-S-lysine were obtained.

$^1$H-NMR (D$_2$O): 1.0–1.4 (tr, 3H); 1.0–2.5 (m, 9H); 2.5–4.4 (m, 9H); 3.9–4.4 (q, 2H); 4.5–5.0 (m, 1H); 5.1 (s, 2H); 7.1–7.5 (m, 10H).

(3) Benzyl N$_\alpha$-(1-S-carbethoxy-3-phenyl-propyl)-N$_\epsilon$-benzyloxycarbonyl-S-lysyl-cis,endo-2-azabicyclo-[3.3.0]-octane-3-S-carboxylate (a) 560 mg of benzyl 2-azabicyclo-[3.3.0]-octane-3-carboxylate hydrochloride prepared according to Example I(3) were reacted with 940 mg of N$_\alpha$-(1-S-carbethoxy-3-phenyl-propyl)-N$_\epsilon$-benzyloxycarbonyl-S-lysine prepared according to Example VIII(2), analogously to Example I(4). After the mixture had been worked up, 1.5 g of an oil, which was a mixture of two diastereomeric compounds, were obtained.

The diastereomer mixture was separated into the individual components by column chromatography with silica gel and cyclohexane/ethyl acetate 2:1 as the eluting agent. The isomer eluted first was the above compound. 0.6 g of an oil was obtained.

$^1$H-NMR (CDCl$_3$) (after replacement of H by D with D$_2$O): 1.0–2.6 (m, 20H); 2.6–4.5 (m, 8H); 4.6–5.0 (m, 2H); 5.1–5.3 (double s., 4H); 7.1–7.6 (m, 15H).

(b) The later eluate gave 0.4 g of benzyl N$_\alpha$-(1-S-carbethoxy-3-phenyl-propyl)-N$_\epsilon$-benzyloxycarbonyl-S-lysyl-cis,endo-2-azabicyclo-[3.3.0]-octane-3-R-carboxylate.

$^1$H-NMR (CDCl$_3$) (after replacement of H by D with D$_2$O): 1.0–2.6 (m, 20H); 2.6–4.4 (m, 8H); 4.5–5.0 (m, 2H); 5.1–5.3 (double s., 4H); 7.1–7.5 (m, 15H).

(4) N$_\alpha$-(1-S-Carbethoxy-3-phenyl-propyl)-S-lysyl-cis,endo-2-azabicyclo-[3.3.0]-octane-3-S-carboxylic acid dihydrochloride 500 mg of benzyl N$_\alpha$-(1-S-carbethoxy-3-phenyl-propyl)-N$_\epsilon$-benzyloxycarbonyl-S-lysyl-cis,endo-2-azabicyclo-[3.3.0]-octane-3-S-carboxylate from Example VIII(3a) were dissolved in 20 ml of ethanol and were debenzylated hydrogenolytically under normal pressure, with addition of 0.1 g of 10% Pd/C. When the uptake of hydrogen had ended, the catalyst was filtered off, ethanolic hydrogen chloride solution was added to the ethanolic solution until a pH of 1 was reached, and the ethanol was evaporated off in vacuo. Diisopropyl ether was added to the residue, whereupon the product solidified. 200 mg were obtained.

$^1$H-NMR of the betaine (CDCl$_3$, after replacement of H by D with D$_2$O): 1.0–2.5 (m, 20H); 2.6–4.4 (m, 8H); 4.4–5.1 (m, 2H); 7.2 (s, 5H).

EXAMPLE IX

N-(1-S-Carbethoxy-3-phenyl-propyl)-S-lysyl-cis,endo-2-azabicyclo-[3.3.0]-octane-3-R-carboxylic acid dihydrochloride 0.3 mg of the corresponding benzyl ester from Example VIII(3b) were reacted, and the mixture worked up, analogously to Example VIII(4). 110 mg of the carboxylic acid were obtained in the form of the dihydrochloride.

$^1$H-NMR of the betaine (CDCl$_3$, after replacement of H by D with D$_2$O): 1.0–2.6 (m, 20H); 2.6–4.4 (m, 8H); 4.1–5.1 (m, 2H); 7.2 (s, 5H).

EXAMPLE X

N-(1-S-Carboxy-3-phenyl-propyl)-S-lysyl-cis,endo-2-azabicyclo-[3.3.0]-octane-3-S-carboxylic acid hydrochloride 0.5 g of N-(1-S-carbethoxy-3-phenyl-propyl)-S-lysyl-cis,endo-2-azabicyclo-[3.3.0]-octane-3-S-carboxylic acid dihydrochloride from Example VIII(4) was suspended in 20 ml of dimethoxyethane. Aqueous 4N KOH was added until a pH of 9-10 was reached. The mixture was stirred for half an hour. It was then adjusted to pH 4 with hydrochloric acid and concentrated to dryness in vacuo, the residue was taken up in ethyl acetate and the mixture was filtered. The ethyl acetate solution was concentrated and the residue was triturated with diisopropyl ether, whereupon it solidified.

Yield: 0.35 g.

¹H-NMR (D₂O): 1.2–2.5 (m, 17H); 2.5–4.5 (m, 6H); 4.5–5.0 (m, 2H); 7.2 (s, 5H).

EXAMPLE XI

N_α-(1-S-Carboxy-3-phenyl-propyl)-S-lysyl-cis,endo-2-azabicyclo-[3.3.0]-octane-3-R-carboxylic acid hydrochloride 500 mg of N_α-(1-S-carbethoxy-3-phenyl-propyl)-S-lysyl-cis,endo-2-azabicyclo-[3.3.0]-octane-3-R-carboxylic acid dihydrochloride from Example IX were hydrolyzed, and the mixture was worked up, analogously to Example X.

Yield: 0.32 g.

¹H-NMR (D₂O): 1.2–2.5 (m, 17H); 2.5–4.5 (m, 6H); 4.5–5.0 (m, 2H); 7.2 (s, 5H).

EXAMPLE XII

N-(1-S-Carbethoxy-3-phenyl-propyl)-O-ethyl-S-tyrosyl-cis,endo-2-azabicyclo[3.3.0]octan-3-S-carboxylic acid (1) N-(1-R,S-carbethoxy-3-phenyl-propyl)-O-ethyl-S-tyrosine benzyl ester Analogously to example IV, 24 g ethyl benzoylacrylate dissolved in 100 ml ethanol were reacted with 30 g O-ethyl-S-tyrosine benzyl ester in the presence of 0.5 ml triethylamine. The solution was concentrated, the residue was digested with diethylether petroleum ether (1:1) and dried in vacuo. 42 g of the RS, S-compound were obtained.

(2) N-(1-R,S-carbethoxy-3-phenyl-propyl)-O-ethyl-S-tyrosine 40 g of the product from (1) were dissolved in 800 ml glacial acetic acid and the solution was hydrogenated under 100 bar and room temperature in the presence of 4 g Pd/C (10 percent). After the crude product had been chromatographed over silica gel in the solvent ethyl acetate/cyclohexane 1:3 and the solution had been concentrated to dryness, 25 g of the title compound were obtained, which proved to be almost homogen by thin layer chromatography. Melting point: 205°-213° C.

Analysis:
C₂₃H₃₉NO₅ (399.5)

| | | | |
|---|---|---|---|
| Calculated: | 69.15 C | 7.31 H | 5.30 N |
| Found: | 69.5 | 7.4 | 3.3 |

(3) N-(1-S-carbethoxy-3-phenyl-propyl)-O-ethyl-S-tyrosyl-cis,endo-2-azabicyclo[3.3.0]octan-3-S-carboxylic acid Analogously to example I(4), 5 g of the free benzyl ester, obtained from example I(3) by treating with alkali and extracting with diethylether, were reacted with 8 g of the compound from example XII(2) and 4.4 g dicyclohexyl-carbodiimide in the presence of 2.7 g 1-hydroxybenzotriazole. After subsequent chromatography as described in example I(4) 2.9 g of an oil, which is the intermediate benzyl ester, were obtained.

¹H-NMR- and mass spectra were in accordance with the given structure.

The benzyl ester was dissolved in 50 ml ethanol, Pd (C) was added and hydrogenation was carried out under normal pressure. The mixture was filtered, the filtrate was concentrated, the residue was digested and dried in vacuo. Yield: 2.2 g.

¹H-NMR (CDCl₃): 1.2–3.0 (m, 15H), 1.27 (t, 3H), 1.4 (t, 3H), 3.0–4.3 (m, 4H), 3.8–4.2 (m, 4H), 6.5–7.1 (2d, 4H), 7.3 (s, 5H).

EXAMPLE XIII

N-(1-S-Carbethoxy-3-phenyl-propyl)-O-methyl-S-tyrosyl-cis,endo-2-azabicyclo[3.3.0]octan-3-S-carboxylic acid The compound was prepared from O-methyl-S-tyrosine benzyl ester analogously to the process described in example XII. The ¹H-NMR spectrum is in accordance with the given structure.

What is claimed is:

1. A method for making a compound of the formula

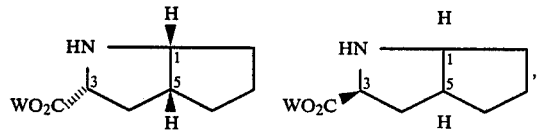

or a salt thereof with an acid or a base, wherein the hydrogen atoms on the bridge-head carbon atoms in the 1- and 5-positions are in the cis-configuration relative to one another and the carboxyl group on the carbon atom in the 3-position is orientated in the endo-position relative to the bicyclic ring system, and wherein W is hydrogen, alkyl having 1–6 carbon atoms, or aralkyl having 7 or 8 carbon atoms, which method comprises cyclizing a compound of the formula

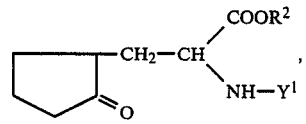

wherein

Y¹ is alkanoyl having 1 to 5 carbon atoms or aroyl having 7 to 9 carbon atoms and R² is alkyl having 1 to 5 carbon atoms or aralkyl having 7 to 9 carbon atoms, with a strong acid, with acylamide and ester cleavage, to give an intermediate compound of the formula

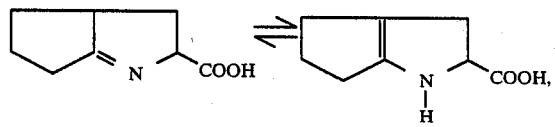

catalytically hydrogenating this intermediate compound to form the desired compound wherein W is hydrogen in the presence of a transition metal catalyst or by reducing said intermediate with a borane-amine complex or a complex borohydride in a lower alcohol, and then optionally esterifying the acid product to give a compound wherein W is alkyl having 1 to 6 carbon atoms or aralkyl having 7 or 8 carbon atoms.

2. A method as in claim 1 wherein said compound of the formula

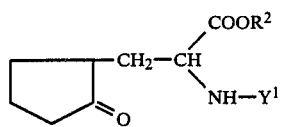

is obtained by reacting an enamine of the formula

wherein $X^1$ is dialkylamino having 2 to 10 carbon atoms or is

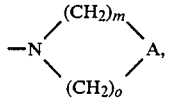

wherein m and o are each integers from 1 to 3 and (m+o)=3 and A is —$CH_2$—, —NH—, —O—, or —S—, with an N-acylated β-halogeno-α-amino-carboxylic acid ester of the formula

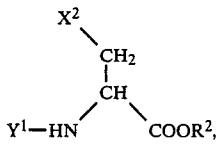

wherein $X^2$ is chlorine or bromine, or with an acrylic acid of the formula

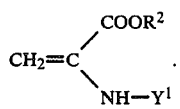

* * * * *

UNITED STATES PATENT AND TRADEMARK OFFICE
CERTIFICATE OF CORRECTION

PATENT NO. : 4,727,160
DATED : February 23, 1988
INVENTOR(S) : Teetz et al.

It is certified that error appears in the above-identified patent and that said Letters Patent is hereby corrected as shown below:

Column 14, lines 25-30 (claim 1, line 2) right-hand formula change

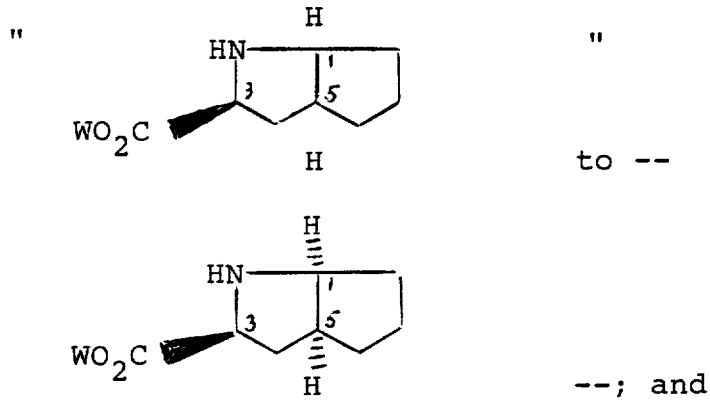

Column 16, line 8 (claim 2, line 10), change "(m+o) = 3" to --(m+o) $\geq$ 3 --.

Signed and Sealed this

Ninth Day of May, 1989

*Attest:*

DONALD J. QUIGG

*Attesting Officer*     *Commissioner of Patents and Trademarks*